(12) United States Patent
Brocchini et al.

(10) Patent No.: US 7,005,454 B2
(45) Date of Patent: *Feb. 28, 2006

(54) POLYMERIC DRUG FORMULATIONS

(75) Inventors: Stephen Brocchini, Highland Park, NJ (US); Stephen R. Hanson, Stone Mountain, GA (US); Joachim B. Kohn, Highland Park, NJ (US)

(73) Assignee: Rutgers, The State University, New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 797 days.

(21) Appl. No.: 09/257,145

(22) Filed: Feb. 24, 1999

(65) Prior Publication Data

US 2002/0019446 A1 Feb. 14, 2002

Related U.S. Application Data

(62) Division of application No. 08/508,577, filed on Jul. 28, 1995, now Pat. No. 5,877,224.

(51) Int. Cl.
*A61K 47/30* (2006.01)
*A61K 47/32* (2006.01)
*A61K 47/34* (2006.01)

(52) U.S. Cl. .............. 514/772.1; 514/772; 514/772.3; 424/486

(58) Field of Classification Search ........... 424/486; 514/955, 802, 772.3, 772, 772.1
See application file for complete search history.

(56) References Cited

U.S. PATENT DOCUMENTS

| | | | |
|---|---|---|---|
| 4,166,800 A | * 9/1979 | Fong | 252/316 |
| 4,277,364 A | 7/1981 | Shasha et al. | 252/316 |
| 4,741,872 A | * 5/1988 | DeLuca et al. | 264/4.7 |
| 5,219,564 A | 6/1993 | Zalipsky et al. | 424/78.17 |
| 5,330,768 A | * 7/1994 | Park et al. | 424/401 |
| 5,639,480 A | * 6/1997 | Bodmer et al. | 424/501 |
| 5,877,224 A | * 3/1999 | Brocchini et al. | 514/772.2 |
| 5,968,899 A | * 10/1999 | Sekine et al. | 514/802 |

FOREIGN PATENT DOCUMENTS

| | | |
|---|---|---|
| EP | 0451082 A1 * | 9/1991 |
| WO | WO 90/15620 | 12/1990 |
| WO | WO 99/04766 * | 2/1999 |

OTHER PUBLICATIONS

Sturesson et al., *International Journal of Pharmaceutics*, 89, 235–244 (1993).

\* cited by examiner

*Primary Examiner*—Gollamudi S. Kishore
*Assistant Examiner*—Liliana Di Nola-Baron
(74) *Attorney, Agent, or Firm*—Synnestvedt & Lechner LLP

(57) ABSTRACT

Polymeric drug formulations containing a non-releasing single-phase dispersion of a water-soluble drug in a water-insoluble tissue-compatible polymer matrix. Polymeric drug formulations are also disclosed containing a single-phase dispersion of a water-soluble drug and a water-insoluble tissue-compatible polymer matrix, and a second, phase-disrupting polymer that is non-miscible with the tissue-compatible polymer and is present in an amount sufficient to form phase-separated microdomains of the second polymer in the tissue-compatible polymer matrix, so that the release rate of the water-soluble drug from the tissue-compatible polymer matrix is related to the amount of the second polymer. Methods of preparing the polymeric drug formulations are also described, as well as methods for site-specific drug delivery utilizing the polymeric drug formulations.

29 Claims, No Drawings

POLYMERIC DRUG FORMULATIONS

CROSS REFERENCE TO RELATED APPLICATION

This is a divisional of U.S. patent application Ser. No. 08/508,577 filed Jul. 28, 1995, which issued as U.S. Pat. No. 5,877,224 on Mar. 2, 1999. The disclosure of this application is incorporated herein by reference.

BACKGROUND OF THE INVENTION

The present invention relates to polymeric drug formulations in the form of solid single-phase dispersions of water-soluble drugs in water-insoluble tissue-compatible polymer matrices. The present invention additionally relates to solid single-phase dispersions of water-soluble drugs in water-insoluble tissue-compatible polymer matrices that include a second, phase-disrupting polymer so that phase-separated microdomains form in the matrices, which results in the release rate of the drug from the polymer matrix being affected by the amount of the second polymer present.

The present invention also relates to methods for forming the polymeric drug formulations of the present invention in which the water-soluble drug, the water-insoluble tissue-compatible polymer and, optionally, the second phase-disrupting polymer are dissolved in a common solvent and then coprecipitated by the addition to the solution of a carefully selected non-solvent. The resulting coprecipitate is in the form of a solid single-phase dispersion of the drug and polymer with the second polymer, when present, being concentrated in phase-separated microdomains. The present invention also relates to methods for site-specific drug delivery by implanting in the body of a patient in need thereof the polymeric drug formulations of the present invention.

In the context of this invention, a water-soluble drug is defined as a hydrophilic compound with a solubility in water greater than 1 percent (w/v) and that is practically insoluble in nonpolar organic solvents such as ethyl acetate, methylene chloride, chloroform, toluene, or hydrocarbons. Peptide-based drugs represent a particularly important class of water-soluble drugs as defined here.

When such water-soluble drugs are incorporated into polymers, it is often difficult to prevent the rapid, uncontrolled release of drug in a burst-like fashion from the drug-polymer matrix. This is known as the "burst effect". The burst effect becomes particularly noticeable at high drug loadings. Within the context of this invention, high levels of drug loading are defined as drug loadings in excess of 10 percent (w/w) based on the weight of drug contained per 100 mg of drug-polymer matrix. The term "lag effect" refers to the phenomenon that the rate of drug release from a drug-polymer matrix decreases to zero or close to zero, e.g., the release of drug stops for a certain period of time. Burst effects and lag effects are some of the commonly observed phenomena that render drug-polymer matrices unsuitable as "controlled release systems" for clinical applications.

The physical state of the drug-polymer mixture, also referred to as the morphology of the system, is an often overlooked key parameter in the design of polymeric drug delivery systems. In the context of the present invention, one can distinguish between the following fundamentally different morphological states: single-phase dispersions and multi-phase dispersions.

In single-phase dispersions the drug is dispersed within the polymeric phase on a molecular scale. Within the context of this invention, a single-phase dispersion is defined as a drug-polymer matrix that appears transparent and clear to transmitted visible light. This simple requirement indicates that the drug-polymer matrix is free of microdomains on the length-scale of visible light and therefore does not scatter transmitted visible light. The formation of a single-phase dispersion requires not only that the drug and polymer have some mutual miscibility, but requires also a method for creating a molecular dispersion of the drug within the polymeric phase. This is an important, often overlooked point: If a drug and polymer particles are simply mixed without creating a molecular dispersion of the drug in the polymer matrix, a single-phase dispersion cannot form, even if drug and polymer are mutually miscible.

In multi-phase dispersions, phase-separated domains exist within the drug-polymer matrix. In multi-phase dispersions, microdomains having dimensions on the length scale of visible light may be present. Within the context of the present invention, such dispersions are readily discerned by the property that the drug-polymer matrices are translucent to visible light, but appear hazy, cloudy, or foggy. Alternatively, the drug may be present in the form of distinct particles or crystals readily discernible by microscopic examination of the drug-polymer matrix. In the extreme case, the drug may be embedded within the polymer in the form of macroscopic particles, readily visible upon inspection by the naked eye.

Hydrophobic polymer matrices of both degradable and nondegradable polymers have been studied as potential vehicles for drug delivery. Although this invention is applicable to both degradable and nondegradable polymers, the following discussion is focused on the more complex degradable systems since the theory of drug release from nondegradable systems is well-known to those skilled in the art. In addition, degradable drug release formulations are generally recognized as particularly useful as implants for the delivery of peptide drugs, which, because of their low oral bioavailabilities and short half-lives in plasma, cannot be administered by conventional oral and parenteral routes.

Release characteristics from degradable polymer matrices are influenced by several factors, the most important factors being drug loading, the physical state of the drug within the polymeric matrix, and the rate of polymer degradation and erosion as determined by the composition, morphology, and molecular structure of the polymeric matrix.

Drug loading affects the release mechanism and release rate. In the prior art, the simple case of a multi-phase dispersion in which drug particles are dispersed within the polymeric phase is well understood. Briefly, at low loadings, individual drug particles have no contact between each other. Water and/or drug molecules must diffuse through the polymer matrix to allow drug release, which consequently leads to slow release. Drug particles entrapped within the polymeric matrix may not be released at all until polymer degradation leads to the physic al erosion of the polymeric matrix. At high loadings, individual drug particles are in physical contact with each other and the dissolution of individual particles results in the formation of discrete pores within the polymeric matrix through which drug is released by slow diffusion (see Siegel and Langer, *J. Control. Rel.,* 14, 153–67 (1990)).

Often, the effect of drug loading is much more complex since the loading level will influence the morphology of the drug-polymer matrix. This point is often overlooked in the prior art. If a drug is only partially miscible with the polymer, a single-phase dispersion may be formed at low loadings. However, as the loading level is raised above the limited miscibility between the drug and the polymer, multi-phase dispersions are formed. At this point, a dramatic difference in the release mechanism is usually observed. The release rates and mechanisms are particularly difficult to analyze in formulations in which some fraction of the drug forms a single-phase blend with the polymeric matrix, while another fraction is present in the form of phase-separated domains.

In the prior art it is well-known that control of particle size and homogeneity of the drug dispersion within the polymeric phase is critical in order to obtain reproducible and prolonged drug release profiles. The formulation of polymeric drug delivery devices for water-soluble drugs as defined above is especially challenging because it is difficult to obtain uniformly dispersed mixtures of such drugs within a water-insoluble polymeric phase. This is due to the fact that no single solvents are available capable of dissolving the water-soluble drug and the water-insoluble polymeric matrix simultaneously to form a homogeneous solution from which a uniformly dispersed mixture of drug and polymer may be readily recovered. For that reason, particles of a water-soluble drug are often suspended within a solution of the polymer in an organic solvent such as methylene chloride. Upon solvent casting, the discrete drug particles are embedded within the polymeric phase in a multi-phase dispersion where the exact distribution of the drug particles is difficult to control and difficult to reproduce. This technique cannot lead to the molecular dispersion of the drug within the polymeric matrix. Alternative techniques for the formulation of polymeric controlled release devices for water-soluble drugs require the simultaneous co-extrusion or co-molding of drug particles mixed with polymer particles. Such processes are known in the literature but have significant limitations, namely, the methods are only applicable to drug-polymer combinations that can be thermally processed below the decomposition temperature of the drug. In addition, these techniques result in the aggregation of drug and polymer in discrete domains that result often in undesirable release profiles.

In some cases, careful physical admixture can produce formulations having acceptable release profiles. However, such formulations have release profiles that are complex functions of drug loading levels, size and distribution of drug particles within the polymeric matrix, and the rate of polymer degradation. For example, instead of extending the duration of drug release, elevated drug loadings usually lead to significant burst effects and an increase in the rate of drug release. Thus, it is difficult to design a suitable formulation providing an immediate release of drug at a reproducible and acceptable rate, without burst or lag effects with sustained release over extended periods of time. This is but one example of the design limitations inherent in polymeric drug delivery systems in which the rate of drug release is determined by drug loading, particle size and distribution, and/or polymer degradation.

Sturesson et al., Intern. *J. Pharm.*, 89, 235–44 (1993), added poly(ethylene glycol) (PEG) to a poly(lactic acid-co-glycolic acid) matrix to enhance the drug release rate by providing a system with a greater content of water-soluble substances in the polymer matrix, expecting the material to facilitate polymer hydrolysis and promote diffusional release of the water-soluble drug in the matrix. However, an enhanced rate of drug release was not observed.

A means by which the effects of particle size and distribution on the release profile can be minimized and by which drug release from a polymeric matrix may be controlled independent of drug loading or polymer degradation would be highly desirable.

SUMMARY OF THE INVENTION

This need is met by the present invention. It has now been discovered that the drug release rate from single-phase dispersions of water-soluble drugs in water-insoluble tissue-compatible polymer matrices may be controlled by including a second polymer in the tissue-compatible polymer matrix that is non-miscible with the basic polymer matrix, so that phase-separated microdomains of the second polymer are formed in the drug-polymer matrix.

While not being bound by any particular theory, it is believed that the phase-separated microdomains disrupt the monolithic or homogeneous phase of the single-phase drug-polymer dispersion such that the release rate of the drug from the polymer matrix is related to the amount of phase-disrupting second polymer present. The present invention represents a means by which the drug release profile from a polymer matrix may be modified and fine-tuned independent of the level of drug loading, the drug particle size, the distribution of drug particles within the polymeric matrix, or the degradation rate of the tissue-compatible polymer.

The single-phase dispersions of the present invention of water-soluble drugs in water-insoluble tissue-compatible polymer matrices have the unexpected and surprising property that the drug is not released from the drug-polymer matrix to any appreciable extent, even at high loadings. This property is not anticipated by the teachings in the prior art according to which the incorporation of high loadings of a water-soluble drug should have resulted in the observation of a strong burst effect, swelling (due to water-uptake by the drug-polymer matrix), and the rapid release of most of the drug in contact with the matrix surface. In stead, in the single-phase dispersions of the present intention, drug release occurs only if a second phase-disrupting polymer is added into the formulation.

In the absence of such a phase-disrupting, second polymer, in most instances, the drug will be expressed at the matrix surface without being actually released from the polymeric matrix to any appreciable extent. Such a non-releasing formulation could be useful for some therapeutic applications of water-soluble drugs where the drug is effective as a surface modifying agent. Therefore, according to one aspect of the present invention, a polymeric drug formulation is provided that is a non-releasing single-phase dispersion of a water-soluble drug in a water-insoluble tissue-compatible polymer matrix.

The single-phase dispersions of the present invention are formed by simultaneously dissolving the drug and matrix polymer in an organic solvent system in which the drug and polymer are capable of forming a homogeneous solution. The homgenous solution of drug and polymer can be used directly for the fabrication of coatings, tubes, filaments or films by appropriate fabrication techniques. Alternatively, the homogeneous solution can be precipitated into a carefully selected non-solvent, resulting in the formation of an intimate, molecularly dispersed co-precipitate of drug and polymer.

Therefore, another aspect of the present invention includes a method of forming a single-phase dispersion of a water-soluble drug with a water-insoluble tissue-compatible polymer. This requires that the drug is miscible in the solid phase with the polymer, and that a solvent system can be identified that is capable of forming a homogeneous solution of the drug and polymer, followed by the addition to the homogeneous solution of a carefully selected non-solvent for the drug and polymer so that the drug and polymer coprecipitate from the solution as a solid single-phase dispersion of the drug and polymer. This aspect of the present invention also includes polymeric drug formulations prepared by this method of the invention.

The inclusion of a second phase-disrupting polymer to the drug-polymer matrix to control the drug release profile provides a polymer drug formulation useful in the therapeutic applications of water-soluble drugs in general and peptide-based drugs in particular. Therefore, yet another aspect of the present invention provides a polymeric drug formulation that is a single-phase dispersion of a water-soluble drug in a water-insoluble tissue-compatible polymer matrix, which includes a second, phase-disrupting polymer that is non-miscible with the tissue-compatible polymer and is present in an amount sufficient to form phase-separated microdomains of the second polymer in the tissue-compatible polymer matrix, so that the release rate of the water-soluble drug from the tissue-compatible polymer matrix is related to the amount of the second polymer.

The polymeric drug formulations of the present invention containing a second phase-disrupting polymer are likewise formed by dissolving the tissue-compatible polymer, drug and second phase-disrupting polymer in a solvent system capable of forming a homogeneous solution of all three components. The homogeneous solution can also be directly fabricated to provide coatings, tubes, filaments, films, microspheres or other shaped articles, by appropriate fabrication techniques, or precipitated into a non-solvent to form an intimate, molecularly dispersed mixture of the drug, tissue-compatible polymer, and the second phase-disrupting polymer containing phase-separated microdomains having dimensions on the length scale of the wavelength of visible light.

Therefore, another aspect of the present invention provides a method of forming a polymeric drug formulation by blending a water-soluble drug with a water-insoluble tissue-compatible polymer and a second, phase-disrupting polymer, that is non-miscible with the drug-delivery polymer, in a solvent system capable of forming a homogeneous solution of the drug, the polymer and the second, phase-disrupting polymer, and adding to the solution an amount of a non-solvent for the drug, the tissue-compatible polymer and the second, phase-disrupting polymer, so that a microdomain-separated solid coprecipitate of the drug, the tissue-compatible polymer and the second, phase-disrupting polymer is formed, wherein the second, phase-disrupting polymer is blended in an amount effective to form separated microdomains. This aspect of the present invention likewise includes polymeric drug formulations prepared by this method of the invention.

The polymeric drug formulations of the present invention are intended for use as medical implants. Therefore, still yet another aspect of the present invention provides a method for site-specific drug delivery by implanting in the body of a patient in need thereof the polymeric drug formulations of the present invention.

The polymeric drug formulations of the present invention are particularly useful when formulated with platelet aggregation inhibiting peptide drugs to improve the clinical performance of stents, the small metal springs used to prevent injured arteries from collapsing during or after angioplasty or other cardiovascular procedures. Typically, stents are placed into an artery, but the metal surface will often result in blood clotting at the stent surface and lead to occlusion of the artery. When the polymeric drug formulations of the present invention are loaded with platelet aggregation inhibiting peptide drugs and placed in-between the arterial wall and the stent, the local release of the platelet aggregation inhibiting peptide drug will reduce the tendency of blood to form clots at the implant site.

The present invention can be used to prepare polymeric films containing up to 30 percent by weight of a platelet aggregation inhibiting peptide drug. The films are pliable, deformable, Soft, elastic and translucent, yet are mechanically strong enough to withstand pulling and deformation during handling. Depending on the exact formulation and amount of the phase-disrupting second polymer added into the formulation, the films will release biologically active and chemically pure platelet aggregation inhibiting peptide drugs for periods ranging from several hours to several weeks. The mechanical and release properties of films of the polymeric drug formulations of the present invention containing platelet aggregation inhibiting peptide drugs are ideally suited for placement around an intra-arterial stent.

Methods for site-specific drug delivery in accordance with the present invention therefore include implanting the polymeric drug formulation of the present invention containing a platelet aggregation inhibiting peptide drug during or following a cardiovascular procedure in which a stent is inserted into an artery, by placing a film of the drug formulation between the arterial wall and the stent, so that local release of the platelet aggregation inhibiting peptide drug will reduce the formation of blood clots at the stent insertion site.

Polymeric drug formulations according to the present invention containing platelet aggregation inhibiting peptide drugs are also useful in the formulation of a wider range of medical devices and implants that come in contact with blood. Whenever a blood-contacting device is used for any length of time, the patient has to undergo anticoagulation therapy to prevent the formation of blood clots at the device surface. The acute thrombogenicity of artificial surfaces can be reduced by the release of a platelet aggregation inhibiting peptide drug from the device surface. Therefore, the polymeric drug formulations of the present invention containing an anti-thrombotic peptide drug can be used to form coatings on existing device surfaces by dipping or spray-coating techniques. Specific applications include the reformulation of the surface of vascular grafts, the formulation of new blood bags, and the reduction of the thrombogenic potential of tubings and membranes that come in contact with blood in extracorporeal devices.

Therefore, methods for site-specific drug delivery in accordance with the present invention will also include implanting in the body of a patient a blood-contacting device or implant coated with the polymeric drug formulation of the present invention in which the drug is a platelet aggregation inhibiting peptide drug. The present invention therefore also includes blood-contacting devices or implants coated with the polymeric drug formulation of the present invention in which the drug is a platelet aggregation inhibiting peptide drug.

A more complete appreciation of the invention and many more other intended advantages can be readily obtained by reference to the following detailed description of the preferred embodiment.

DETAILED DESCRIPTION OF THE PREFERRED EMBODIMENT

The polymeric drug formulations of the present invention are based on well-known tissue-compatible polymers.

Depending upon the intended end-use, the tissue-compatible polymer may be Degradable or non-degradable under physiological conditions. The polymer to be used in this invention has to be readily soluble in a wide range of solvents and chemically compatible with the drug to be delivered. Suitable candidate materials for use in this invention are the previously-described degradable poly(carbonates) disclosed by U.S. Pat. No. 5,099,060, the poly(iminocarbonates)i described by U.S. Pat. No. 4,980,449 and the poly(arylates) disclosed by U.S. Pat. No. 5,216,115. The disclosures of all three patents are incorporated herein by reference. The tyrosine dipeptide-derived poly(carbonates), poly(iminocarbonates) and poly(arylates) disclosed therein are preferred, with tyrosine dipeptide-derived poly(arylates) being particularly preferred. The most preferred tyrosine dipeptide derived poly(arylate) is poly(desaminotyrosyl-tyrosine hexyl ester adipate) (poly(DTH adipate)). Poly (DTH adipate) having a weight-average molecular weight ranging between about 80,000 and about 200,000 daltons is particularly preferred.

Other well-known tissue-compatible polymers that may be used include poly(lactic acid), poly(glycolic acid), and co-polymers thereof, poly(ethylene-co-vinyl acetate), (commonly referred to by it abbreviation EVA), poly(caprolactone), poly(orthoesters), poly(vinyl-pyrrolidone), pyran copolymer, poly(hydroxypropyl-methacrylamide-phenol), poly(hydroxyethyl-aspartamide-phenol), poly(ethylene oxide)-poly(lysine) substituted with palmitoyl residues, poly(hydroxybutyric acid), poly(acetals), poly(dihydropyran), poly(cyanoacrylates) and cross-linked and amphipathic block copolymers of hydrogels, and the like. The polymer molecular weight will depend upon the requirements of the intended end use of the polymeric drug formulation. The polymer molecular weight is one factor to be considered for drug compatibility and an appropriate polymer molecular weight can be readily determined by one of ordinary skill in the art without undue experimentation.

In addition to being chemically compatible with the tissue-compatible polymer, drugs for use in the polymeric drug formulations of the present invention must possess at least some solubility in the non-aqueous solvent systems of the present invention and must be chemically stable in the solvent systems. While the polymeric drug formulations are particularly well-suited for the delivery of peptide drugs, non-peptide drugs may be used as well. Examples of suitable non-peptide drugs include natural and unnatural antibiotics, cytotoxic agents, and oligonucleotides.

The polymeric drug formulations in the present invention are particularly well-suited for the delivery of peptide drugs and overcome some of the difficulties encountered in previous attempts to formulate controlled release devices that show reproducible release profiles without burst and/or lag effects, and the premature deactivation of the drug during fabrication of the device. The peptide drugs suitable for formulation with the compositions of the present invention include natural and unnatural peptides, oligopeptides, cyclic peptides, library generated oligopeptides, polypeptides, and proteins, as well as peptide mimetics and partly-peptides, as long as the specific drug moiety has some solubility in a single solvent or solvent mixture such that the drug moiety and the water-insoluble polymer can form a homogenous solution. The peptide drugs may be obtained by some form of chemical synthesis or be naturally produced or be obtained by recombinant genetics, and can range in molecular weight as low as 200 daltons.

Suitable peptide drugs include immunoglobulins and immunoglobulin fragments. Peptide drugs of particular interest include platelet aggregation inhibiting peptides, which are antagonists of the cell surface glycoprotein IIb/IIIa, thus preventing platelet aggregation and ultimately clot formation. Preferred platelet aggregation inhibiting (PAI) peptides include the PAI peptides disclosed by published PCT Application No. WO 90/15620, the disclosure of which is incorporated herein by reference.

The following PAI peptides are particularly preferred:

PAI 1: E-C-A-D-G-L-C-C-D-Q-C-R-F-L-K-K-G-T-V-C-R-V-A-K-G-D-W-N-D-D-T-C-T-G-Q-S-C-D-C-P-R-N-G-L-Y-G

PAI 2: E-E-P-C-A-T-G-P-C-C-R-R-C-K-F-K-R-A-G-K-V-C-R-V-A-K-G-D-W-N-N-D-Y-C-T-G-K-S-C-D-C-P-R-N-P-W-N-G

PAI 3: G-C-G-K-G-D-W-P-C-A-$NH_2$

PAI 4: G-C-K-G-D-W-P-C-A-$NH_2$

PAI 5: C-G-K-G-D-W-P-C-$NH_2$

PAI 7: C-K-G-D-W-C-A-$NH_2$

PAI 9: Mpr-K-G-D-Pen-$NH_2$

PAI 10: C-K-G-D-W-P-C-$NH_2$

PAI 12: C-K-G-D-W-P-C-$NH_2$

PAI 13: C-K-G-D-F-P-C-$NH_2$

PAI 14: C-K-G-D-L-P-C-$NH_2$

PAI 15: C-K-G-D-V-P-C-$NH_2$

PAI 16: C-K-G-D-Y(OMe)-P-C -$NH_2$

PAI 17: C-K-G-D-(2-Nal)-P-C-$NH_2$

PAI 18: C-K-G-D-(Cha)-P-C-$NH_2$

PAI 19: Mpr-K-G-D-W-P-C-$NH_2$

PAI 20: Mpr-K-G-D-Y-P-C-$NH_2$

PAI 21: Mpr-K-G-D-F-P-C-$NH_2$

PAI 22: Mpr-K-G-D-L-P-C-$NH_2$

PAI 23: Mpr-K-G-D-V-P-C-$NH_2$

PAI 24: Mpr-K-G-D-Y(OMe)-P-C-$NH_2$

PAI 25: Mpr-K-G-D-(2-Nal)-P-C-$NH_2$

PAI 26: Mpr-K-G-D-(Cha)-P-C-$NH_2$

PAI 27: cyclo(G-K-G-D-W-P)

PAI 28: cyclo($A^†$K-G-D-W-P)

PAI 29: cyclo (A-K-G-D-W-P)

PAI 30: cyclo(F-K-G-D-W-P)

PAI 31: cyclo(beta-Ala-K-G-D-W-P)

PAI 32: cyclo(gamma-Abu-K-G-D-W-P)

PAI 33: cyclo(R-K-G-D-W-P)

PAI 34: C-K-G-D-W-G-C-$NH_2$

PAI 37: C-K-A-D-W-P-C-$NH_2$

PAI 39: C-K-G-D-W-(Sar)-C-$NH_2$

PAI 41: C-K-G-D-I-P-C-$NH_2$

PAI 42: C-K-G-D-(4-Cl-Phe)-P-$NH_2$

PAI 43: C-K-(Sar)-D-W-P-C-$NH_2$

PAI 44: C-K-G-D-(4-$NO_2$-Phe)-P-C-$NH_2$

PAI 47: Acetyl-C-K-G-D-W-P-C-$NH_2$

PAI 48: Mpr-K-G-D-W(Formyl)-P-C-$NH_2$

PAI 49: Mvl-K-G-D-W-P-C-$NH_2$

PAI 51: Mpr-K-G-D-W-P-Pen-$NH_2$

PAI 52: Mpr-K-G-D-W-P-$Pen^†$-$NH_2$

PAI 54: Mpr-K-G-$D^†$-W-P-Pen-$NH_2$

PAI 55: Mpr-K-G-D-W-(Thz)-C-$NH_2$

PAI 56: Mpr-K-G-D-H (2,4-DNP)-P-C-$NH_2$

PAI 57: Mpr-K-G-D-(2-Nai)-P-Pen-$NH_2$

PAI 58: Mvl-K-G-D-W-P-Pen $NH_2$
PAI 59: Mpr-K-G-D-W-(Pip)-Pen-$NH_2$
PAI 60: Mpr-(Har)-G-D-W-P-C-NH2
PAI 61: Mpr-K-G-D-W-P-$C^\dagger$-$NH_2$
PAI 62: Mpr-$K^\dagger$-G-D-W-P-Pen-$NH_2$
PAI 63: Mpr-(Har)-G-D-W-P -Pen-$NH_2$
PAI 64: Mpr-(Acetimidyl-D-W-P-C-$NH_2$
PAI 65: Mpr-(Acetimidyl-Lys)-G-D-W-P-Pen-$NH_2$
PAI 66: Mpr ($N^G,N^{G'}$-ethylene-Har)-G-D-W-P-C-$NH_2$
PAI 67: Mpr ($N^G,N^{G'}$-ethylene-Har)-G-D-W-P-Pen-$NH_2$
PAI 68: Mpr-Har-Sar-D-W-P-C-$NH_2$
PAI 69: Mpr-(Acetimidyl-Lys)-G-D-W-P-Pen-$NH_2$
PAI 70: Mpr-(Phenylimidyl-Lys)-G-D-W-P-C-$NH_2$
PAI 71: Mpr-Har-Sar-D-W-P-Pen-$NH_2$
PAI 72: Mpr-(Phenylimidyl-Lys)-G-D-W-P-Pen-$NH_2$
PAI 73: Mpr-Har-G-D-W-(3,4-dehydro-Pro)-C-$NH_2$
PAI 74: Mpr-Har-G-D-Pen-$NH_2$
PAI 75: Mpr-(Phenylimidyl-Lys)-G-D-Pen-$NH_2$ PAI peptides are chemically compatible with poly(DTH adipate) disclosed by U.S. Pat. No. 5,216,115. Pliable, deformable, soft, elastic and transparent films of poly(DTH adipate) containing up to 30 percent by weight of PAI peptides can be produced according to the methods of the present invention.

The chemical compatibility of drugs with tissue-compatible polymers can be readily determined by one of ordinary skill in the art without undue experimentation. Methods to evaluate chemical compatibility between the polymer and a drug moiety have been described for the case of polyanhydrides by K. W. Leong, P. D. Amore, M. Marlett, and R. Langer, *J. Biomed. Mater. Res.*, 20, 51–64 (1986). These methods are generally applicable and involve the fabrication of drug-loaded polymeric matrices by several techniques, followed by the evaluation of polymer molecular weight, drug purity, and the identification of any newly formed chemical species by HPLC, FT-IR or other analytical techniques.

An important issue is the evaluation of mutual miscibility between the polymer and the drug. According to the present invention, the drug moiety and the polymeric matrix must be miscible (blendable) in the solid state. The theoretical criteria (as well-known to anyone skilled in the art-see Billmeyer, *Textbook of Polymer Science*) for miscibility is a shift in the polymer glass transition temperature upon mixing of the drug with the polymer. An empirical criteria, as defined here within the context of this invention, is that upon solvent casting, extrusion, or compression molding a mixture of polymer and drug, a transparent device is obtained that is free of discrete drug particles visible to the naked eye. Transparency of the device indicates that the drug loaded polymeric matrix does not contain phase separated microdomains on the length scale of visible light, while a translucent device having a foggy, cloudy, or hazy appearance can be assumed to contain phase-separated microdomains on the length scale of visible light.

The polymer drug formulations of the present invention may contain drug loadings from trace levels to about 50 percent by weight. Higher drug loadings will be useful only in rare circumstances. Preferably, the compositions contain a therapeutically effective amount of the drug. Drug loading levels of about 30 percent by weight may be employed without detracting from the mechanical properties of films and coatings formed from the compositions of the present invention. Most preferred embodiments are expected to have drug loadings from about 10 to 20 percent by weight.

The polymeric drug formulations of the present invention may optionally include a second, phase-disrupting polymer that is non-miscible with the tissue-compatible polymer. The term "non-miscible" is used in its ordinary sense with respect to the two polymers as defined by Billmeyer, *Textbook of Polymer Science* (3rd Ed., John Wyley & Sons, 1984).

One of ordinary skill in the art can easily select a second, phase-disrupting polymer that is non-miscible with a tissue-compatible polymer without undue experimentation. As a general rule, since the tissue compatible matrix polymer is water-insoluble, water-soluble polymers are good candidates for use as phase-disrupting polymers since these materials will usually be non-miscible with the matrix polymer. Water-solubility is additionally expected to be a favorable property for the phase disrupting polymer since it can enhance the observed release rate of the drug from the drug-polymer matrix. Examples of suitable non-miscible polymers include poly(alkylene oxides) such as poly (ethylene glycol) (abbreviated: PEG), polysaccharides, poly (vinyl alcohol), polypyrrolidone, poly(acrylic acid) and its many water-soluble derivative such as poly(hydroxyethyl-methacrylate), and the like. The present invention also contemplates the use of non-polymeric materials that are non-miscible with the tissue-compatible polymer and result in the formation of phase-separated microdomains.

As a general rule, the exact molecular weight of the phase-disrupting polymer is not a critical parameter and needs to be determined on a trial and error basis, using phase-disrupting polymer preparations of different molecular weights and observing the resulting release profiles. However, this can be performed by one of ordinary skill in the art without undue experimentation.

Molecular weights in the range of about 1,000 daltons to several hundred thousand daltons are useful. One of ordinary skill in the art can determine the optimal molecular weight of the phase-disrupting polymer needed to obtain the required release profile suitable for any given medical application. PEG is particularly well suited for use in combination with poly(DTH adipate) and PAI peptide. PEG having a weight-average molecular weight ranging between about 1,000 and about 2,000 daltons is particularly preferred. When PEG is used as the second phase-disrupting polymer, it should be present at a level between about 2 and about 30 percent by weight. A level between about 5 and about 15 percent by weight is preferred, with a level of about 10 percent by weight being most preferred.

As the concentration of the second, phase-disrupting polymer increases in the formulation, the rate of drug release from the polymer matrix will also increase, although this relationship is not linear. The drug release rate selected will depend upon the therapeutic dosage profile required for the drug to be delivered. However, this also can be readily determined by one of ordinary skill in the art without undue experimentation.

The polymeric drug formulations of the present invention are prepared by simultaneously dissolving the tissue-compatible polymer, drug and optional second, phase-disrupting polymer in an organic solvent system capable of forming a homogenous solution of the tissue-compatible polymer, drug and second polymer, if present. Typical solvent systems will include one or more solvents selected from methanol, methylene chloride, ethanol, ethylene glycol, glycerol, tetrahydrofuran, ethyl acetate, acetonitrile, acetone, diisopropyl ether, methyl t-butyl ether, chloroform, carbon tetrachloride, dichloroethane, and water. Individual drug and polymer components must possess a solubility in at least one of the solvents of at least 1 g/l. The solvents may be pre-blended before the drug and the polymer(s) are dissolved therein. Alternatively, drug or polymer may be dissolved in the individual solvent in which it is most soluble, after which the solutions are combined to form a solvent system in which the drug and polymer(s) are dissolved.

The drug and polymer(s) should be dissolved in the mixing solvents at a level preferably between about 1 and about 30 percent by weight, and preferably between about 5 and about 20 percent by weight. A concentration between about 5 and about 10 percent by weight is most preferred.

The relative solubilities of the drugs and polymers intended for use with the present invention in various organic solvents are well-known chemical properties. The selection of an organic solvent system in which a drug, a tissue-compatible polymer and optionally a second, phase-disrupting polymer are forming a homogeneous solution at their respective concentrations may be readily determined without undue experimentation.

Briefly, using the known solubility profiles of each individual component, one would first consider a simple mixture of each of the individual solvents. For example, if the drug has some solubility in acetone, the phase-disrupting polymer is soluble in methanol, and the tissue compatible polymer is soluble in methylene chloride, a mixture of acetone, methanol, and methylene chloride would be the initial starting point for the development of a solvent system that can dissolve all three of the components in a homogenous solution. Next, hydrogen bonding effects, polarity effects, and common solvent effects are considered. Inspection of the well-known solubility parameters (as listed in any comprehensive solvent information source such as the *CRC Handbook of Physics and Chemistry*) also assists in finding suitable solvent mixtures for all three solutes. The identification of complex solvent mixtures for different solutes is a well-known task in the formulation of numerous pharmaceutical and cosmetic products and can be readily accomplished by anyone skilled in the art.

Compositions in accordance with the present invention in which a PAI peptide is the drug, poly(DTH adipate) is the tissue-compatible polymer and PEG is the second, phase-disrupting polymer, may be prepared by dissolving the PAI peptide and PEG in separate quantities of methanol, which solutions are then combined. The poly(DTH adipate) may then be dissolved in methylene chloride, with the methylene chloride solution then being combined with the methanol solution.

The solution of drug and polymer(s) is then precipitated into a non-solvent to form the sold single-phased dispersion of the drug in the tissue-compatible polymer, optionally including phase-separated microdomains caused by the presence of the second phase-disrupting polymer. The non-solvent should be miscible with the solvents which were used to dissolve drug and polymer(s). Using a non-solvent for the precipitation that is not fully miscible with each of the solvents used to dissolve drug and polymers carries the danger of obtaining a separation of the solvent mixture into two phases during the precipitation process. Although this may be acceptable in some circumstances, this is not the preferred mode of conducting the precipitation step. For example, during early experiments, a homogeneous solution of a peptide drug and a polymer was dissolved in a mixture of methanol and methylene chloride. When this homogeneous solvent mixture was added into hexane used as the precipitation non-solvent, the solvent mixture separated into two layers since methanol and hexane are not fully miscible in all proportions. This prevented the precipitation of a suitable single-phase drug-polymer matrix. Examples of suitable non-solvents include ethers such as diethyl ether, diisopropyl ether, methyl t-butyl ether, and the like, as well as methyl ethyl ketone, acetone, ethyl acetate, acetonitrile, toluene, xylene, carbon tetrachloride and the like. A copious excess of the non-solvent of at least between 5–10 volumes compared to the volume of the dissolving solvents should be employed, and the non-solvent may be chilled as low as the freezing point of the non-solvent to promote the co-precipitation.

The coprecipitated drug-polymer matrices are dried to remove any residual solvent and are then fabricated by known methods to produce a variety of useful articles. Depending on the thermal stability of the drug and the polymer, the articles can be shaped by conventional polymer-forming techniques such as extrusion, compression molding, injection molding and the like to form implantable drug delivery devices.

Poly(DTH adipate) films containing between trace amounts and 30 percent by weight of PAI peptides (as the drug) and between trace amounts and about 30 percent by weight of PEG (as the phase-disrupting polymer) can be inserted between an arterial stent and artery wall to prevent blood clotting at the stent surface and the consequential arterial occlusion. The same composition can also be formed as a coating on the surface of medical devices and implants that come in contact with blood by conventional dipping or spray coating techniques to prevent the formation of blood clots on the device or implant surface. Implantable drug delivery devices formed from the polymeric drug formulations of the present invention may otherwise be implanted in the body of a patient in need thereof for site-specific drug delivery by procedures that are essentially conventional and well-known to those of ordinary skill in the art.

In the management of thrombotic disorders the polymeric drug formulations of this invention may be utilized in a variety of shaped articles. Subjects in need of treatment (typically mammalian) using the polymeric drug formulations of this invention can be administered drug dosages that will provide optimal efficacy. The dose and method of administration will vary from subject to subject and be dependent upon such factors as the type of mammal being treated, its sex, weight, diet, concurrent medication overall clinical condition, the particular compounds employed, the specific use for which these compounds are employed, and other factors which those skilled in the medical arts will recognize.

The polymeric drug formulations of this invention may be prepared for storage under conditions suitable for the preservation of drug activity as well as maintaining the integrity of the polymers, and are typically suitable for storage at ambient or refrigerated temperatures.

The drug components to be incorporated in the polymeric drug formulations of this invention may be provided in a physiologically acceptable carrier, excipient, stabilizer etc., and may be provided in sustained release or timed release formulation supplemental to the polymeric formulation prepared in this invention. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as poly (vinylpyrrolidinone), amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compositions of this invention to be used for therapeutic administration must be sterile. Sterility is readily accomplished by filtration through sterile membranes, or by other conventional methods such as irradiation or treatment with gases or heat. The pH of the compositions of this invention typically will be between 3 and 11, and more preferably from 5 to 9.

While the preferred route of administration for the cardiovascular applications of the polymeric drug formulations of this invention is by surgical implantation of a shaped article or film into a blood vessel, other methods of administration are also anticipated such as subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches.

The compounds of this invention may also be administered in the form of liposome delivery systems, such as small unilamellar vesicles, large unilamellar vesicles and multilamellar vesicles.

The polymeric drug formulations of this invention are suitable for applications where localized drug delivery is desired, as well as in situations were a systemic delivery is desired.

The drugs incorporated into the formulations of this invention may desirably further incorporate agents to facilitate their delivery systemically to the desired drug target, as long as the delivery agent meets the same eligibility criteria as the drugs described above. The active drugs to be delivered may in this fashion be incorporated with antibodies, antibody fragments, growth factors, hormones, or other targeting moieties, to which the drug molecules are coupled.

The polymeric drug formulations of this invention may be formed into shaped articles, such as valves, stents, tubing, prostheses and the like.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these cardiovascular conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

Certain preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

Certain of the polymeric formulations of the present invention, incorporating cardiovascular drugs, prepared and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the polymeric cardiovascular drug formulation embodiments of this invention can be used in any environment in which it is desired that blood coagulation be inhibited, e.g., by incorporation into material such as vascular grafts, stents, orthopedic prostheses, cardiac stents, valves and prostheses, extra corporeal circulation systems and the like.

While many of the embodiments discussed above describe incorporation of drugs having cardiovascular effects, the invention is not so limited. Practically any therapeutic agent having water-solubility and other characteristics suitable for the practice of this invention, for a variety of therapeutic applications are acceptable.

The following non-limiting examples set forth herein below illustrate certain aspects of the invention. All parts and percentages are by weight unless otherwise noted and all temperatures are in degrees Celsius. The PAI peptide was obtained from COR Therapeutics of South San Francisco, Calif. Poly(DTH adipate) was prepared according to the procedure provided in Example No. 2 of U.S. Pat. No. 5,216,115. PEG was obtained from Aldrich Chemicals Milwaukee, Wis. The drug and polymers were used without further purification. Solvents were of "HPLC grade" and were obtained from Fisher Scientific, Pittsburgh, Pa.

EXAMPLES

The following examples are divided into two sections. In the section labeled as "Preferred Methods," the teachings disclosed in this invention are used to prepare release formulations with different release rates. In the second section, labeled as "Comparative Examples," methods known in the prior art are used to prepare similar release devices as those described in the first section. However, the release data obtained demonstrate that the methods known in the prior art provided significantly less suitable release profiles.

Preferred Methods

Example 1

Preparation of a PAI Peptide Containing Release Device with 10 Weight Percent Loading of PEG ($M_w$=1,000 da) and 30 Weight Percent Loading of PAI Peptide Using the Most Preferred Methods Precipitation One of the above-listed PAI peptides (0.16 g) and PEG (0.057 g; $M_w$=1,000) were each dissolved in methanol (7.0 ml and 1.0 ml respectively) Poly(DTH adipate) (0.32 g, $M_w$=110,000) was dissolved in methylene chloride (7.0 ml). The peptide solution was pipetted into the PEG solution, then this mixture was pipetted into the poly(DTH adipate) solution. The resulting homogeneous solution was then dripped into stirred diethyl ether (140 ml) which was cooled by a dry ice-acetone bath. A white flocculent precipitate was formed which was isolated by careful filtration using a sintered glass funnel. After drying under a high vacuum at ambient temperature, 0.43 g of white solid material was recovered.

Film Fabrication

The completely dried PAI peptide-PEG-poly(DTH adipate) precipitate (0.43 g) was carefully cut on a clean dry surface into small pieces and transferred to a mold (4.0 cm×4.0 cm×0.1 mm, polished stainless steel surface). No release substances were applied to the mold. The material was compression molded into a film of a thickness in the range of 0.10–0.15 mm with the compression cycle shown in Table I. Upon removal from the mold, the film was translucent and pliable.

TABLE I

COMPRESSION MOLDING FABRICATION CYCLE FOR THE PREPARATION OF FILMS CONSISTING OF PAI PEPTIDE-PEG-POLY(DTH ADIPATE)

| TEMPERATURE (° C.) | PRESSURE (psi) | TIME (MINUTES) |
|---|---|---|
| Ambient to 95° | 300 | 7 |
| 95° | 6000 | 6 |
| 95–21° | 6000 | 20 |

Total PAI Peptide Loading

Three pieces (total recorded weight of 5–6 mg) were cut from different regions of PAI peptide loaded film and placed into a 10 ml volumetric flask. Tetrahydrofuran (0.5 ml) was added to dissolve the polymer and to liberate the entrapped PAI peptide. After the pieces of film had completely disintegrated and a white solvent was evident, the volumetric flask was filled to the 10 ml level with phosphate buffer (9.5 ml) and gently agitated. An aliquot (1 ml) was pipetted from the flask, filtered (0.45 µm syringe filter), and analyzed for PAI peptide content by HPLC. The experimentally determined amount of PAI peptide found in the films was within ten percent of the theoretically expected amount.

PAI Peptide In-Vitro Release

A device (9.97×15.6 mm, 55.1 mg) was cut from a PAI peptide-PEG-poly(DTH adipate) film, placed into a capped vial containing phosphate buffer (10 ml, 37° C.), and incubated in a shaker bath. After 15 minutes, the device was transferred using forceps to another capped vial containing phosphate buffer (10 ml, 37° C.) and the device was further incubated in the shaker bath. This process was repeated every 15 minutes for the first hour, every 30 minutes for the second hour, then hourly until four hours. The device can be further incubated in phosphate buffer if longer time points are desired. Aliquots of the respective release media (1 ml) were removed from each vial, filtered, and the PAI peptide content was assayed by HPLC analysis. The release profile is compiled in Table II.

TABLE II

24-HOUR IN VITRO RELEASE PROFILE OF PAI PEPTIDE FROM A DEVICE FORMULATED WITH 10 WEIGHT PERCENT OF PEG($M_w$ = 1,000 da) AND 30 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 15 | 1.82 | 1.82 | 11.03 | 11.03 | 0.586 | 39.09 |
| 30 | 0.39 | 2.22 | 2.39 | 13.43 | 0.127 | 8.48 |

TABLE II-continued

24-HOUR IN VITRO RELEASE PROFILE OF PAI PEPTIDE
FROM A DEVICE FORMULATED WITH 10 WEIGHT PERCENT OF
PEG($M_W$ = 1,000 da) AND 30 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 45 | 0.25 | 2.47 | 1.53 | 14.95 | 0.081 | 5.41 |
| 60 | 0.14 | 2.61 | 0.87 | 15.82 | 0.046 | 3.07 |
| 90 | 0.17 | 2.79 | 1.07 | 16.89 | 0.056 | 1.90 |
| 120 | 0.17 | 2.96 | 1.04 | 17.93 | 0.055 | 1.84 |
| 180 | 0.21 | 3.17 | 1.27 | 19.20 | 0.067 | 1.13 |
| 240 | 0.26 | 3.44 | 1.61 | 20.81 | 0.085 | 1.43 |
| 480 | 0.38 | 3.82 | 2.32 | 23.14 | 0.123 | 0.51 |
| 1440 | 0.77 | 4.59 | 4.65 | 27.78 | 0.247 | 0.26 |

The translucent and foggy appearance of the film indicated that phase-separated microdomains had formed. In this study, the targeted minimum release rate for PAI peptide was 0.2 micrograms/cm$^2$min. Release rates between 0.01 and 100 micrograms/cm$^2$min are suitable for use in the present invention. Release rates between 0.10 and 10 micrograms/cm$^2$min are preferred. Table II illustrates that this formulation surpassed the minimum release rate throughout the 24-hour release study. The burst effect was significantly reduced compared to formulations prepared according to procedures known in the prior art.

Example 2

Preparation of a PAI Peptide Containing Release Device with 7 Weight Percent Loading of PEG ($M_w$=1,000 da) and 30 Weight Percent Loading of PAI Peptide Using the Most Preferred Methods Precipitation PAI peptide (0.4 g) and PEG (0.100 g; $M_w$=1,000) were each dissolved in methanol (10.0 ml and 1.0 ml respectively). Poly(DTH adipate) (0.84 g, $M_w$=110,000) was dissolved in methylene chloride (10.0 ml). The PAI peptide solution was pipetted into the PEG solution, then this mixture was pipetted into the poly(DTH adipate) solution. The resulting homogeneous solution was then dripped into stirred diethyl ether (150 ml) which was cooled by a dry ice-acetone bath. A white flocculent precipitate was formed which was isolated by careful filtration using a sintered glass funnel. After drying under high vacuum at ambient temperature 1.04 g of a white solid material was recovered.

Film Fabrication

The completely dried PAI peptide-PEG-poly(DTH adipate) precipitate (0.40 g) was fabricated into a compression molded film as described in Example 1, using the compression profile shown in Table I. Upon removal from the mold, the film was translucent and pliable. Total PAI peptide loading was confirmed by HPLC analysis.

PAI Peptide In-Vitro Release

A device (4.88×11.90 mm, 11.3 mg) was cut from a PAI peptide-PEG-poly (DTH adipate) film loaded with 30 weight percent PAI peptide and 7 weight percent PEG. The release of PAI peptide was determined over a 17-hour period as described in Example 1. The release data are summarized in Table III.

TABLE III

17-HOUR IN VITRO RELEASE PROFILE
OF PAI PEPTIDE FROM A DEVICE FORMULATED
WITH 7 WEIGHT PERCENT OF PEG ($M_W$ = 1,000 da) AND
30 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 15 | 0.17 | 0.17 | 5.08 | 5.08 | 0.14 | 9.55 |
| 30 | 0.04 | 0.21 | 1.29 | 6.37 | 0.04 | 2.42 |
| 60 | 0.09 | 0.30 | 2.72 | 9.09 | 0.07 | 2.55 |
| 300 | 0.12 | 0.42 | 3.74 | 12.83 | 0.10 | 0.44 |
| 1020 | 0.14 | 0.56 | 4.24 | 17.07 | 0.12 | 0.17 |

Table III illustrates that the release rate for PAI peptide was significantly lower in this example than in Example 1. This is in accordance with the teachings of this invention and illustrates that the release rate decreases when the amount of second, phase-disrupting polymer added into the formulation is reduced.

Example 3

Preparation of a PAI Peptide Containing Release Device with 14 Weight Percent Loading of PEG ($M_w$=1,000 da) and 30 Weight Percent Loading of PAI Peptide Using the Most Preferred Methods Precipitation PAI peptide (0.2 g) and PEG (0.097 g; $M_w$=1,000) were each dissolved in methanol (7.0 ml and 1.0 ml respectively). Poly(DTH adipate) (0.37 g, $M_w$=110,000) was dissolved in methylene chloride (7.0 ml). The PAI peptide solution was pipetted into the PEG solution, then this mixture was pipetted into the poly(DTH adipate) solution. The resulting homogeneous solution was then dripped into stirred diethyl ether (140 ml) which was cooled by a dry ice-acetone bath. A white flocculent precipitate was formed which was isolated by careful filtration using a sintered glass funnel. After drying under high vacuum at ambient temperature, 0.54 g of a white solid material was recovered.

Film Fabrication

The completely dried PAI peptide-PEG-poly(DTH adipate) precipitate (0.45 g) was fabricated into a compression molded film as described in Example 1, using the compression profile shown in Table I. Upon removal from the mold, the film was translucent and pliable. Total PAI peptide loading was confirmed by HPLC analysis.

PAI Peptide In-Vitro Release

A device (1.25×2.00 cm, 81.4 mg) was cut from an PAI peptide-PEG-poly(DTH adipate) film loaded with 30 weight percent PAI peptide and 14 weight percent PEG. The release of PAI peptide was determined over a 2-hour period as described in Example I. The release data are summarized in Table IV.

TABLE IV

2-HOUR IN VITRO RELEASE PROFILE OF PAI PEPTIDE
RELEASE FROM A DEVICE FORMULATED WITH 14 WEIGHT
PERCENT OF PEG ($M_W$ = 1,000 da) AND 30 WEIGHT PERCENT
OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 15 | 13.56 | 13.56 | 55.58 | 55.58 | 2.72 | 180.81 |
| 30 | 1.88 | 15.44 | 7.70 | 63.28 | 0.37 | 25.06 |

TABLE IV-continued

2-HOUR IN VITRO RELEASE PROFILE OF PAI PEPTIDE RELEASE FROM A DEVICE FORMULATED WITH 14 WEIGHT PERCENT OF PEG ($M_W$ = 1,000 da) AND 30 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 45 | 0.57 | 16.01 | 2.35 | 65.63 | 0.11 | 7.65 |
| 60 | 0.23 | 16.25 | 0.97 | 66.60 | 0.05 | 3.16 |
| 90 | 0.35 | 16.61 | 1.46 | 68.06 | 0.07 | 2.37 |
| 120 | 0.15 | 16.76 | 1.63 | 68.69 | 0.03 | 1.02 |

Table IV illustrates that the release rate for PAI peptide was significantly increased in this example in comparison to Example 1. This is in accordance with the teachings of this invention and illustrates that the release rate increases when the amount of second, phase-disrupting polymer added into the formulation is increased.

Example IV

Preparation of a PAI Peptide Containing Release Device Containing a 30 Weight Percent Loading of PAI Peptide and a 14 Weight Percent Loading of PEG ($M_w$=20,000 da) Using the Most Preferred Methods Precipitation PAI peptide (0.2 g) land PEG (0.097 g; $M_w$=20,000 da) were each dissolved in methanol (7.0 ml and 1.0 ml respectively). Poly(DTH adipate) (0.37 g, $M_w$=110,000) was dissolved in methylene chloride (7.0 ml). The PAI peptide solution was pipetted into the PEG solution, then this mixture was pipetted into the poly(DTH adipate) solution. The resulting homogeneous solution was then dripped into stirred diethyl ether (140 ml) which was cooled by a dry ice-acetone bath. A white flocculent precipitate was formed which was isolated by careful filtration using a sintered glass funnel. After drying under high vacuum at ambient temperature 0.59 g of a white solid material was recovered.

Film Fabrication

The completely dried PAI peptide-PEG-poly(DTH adipate) precipitate (0.43 g) was fabricated into a compression molded film as described in Example 1, using the compression profile shown in Table I. Upon removal from the mold, the film was translucent and pliable. Total PAI peptide loading was confirmed by HPLC analysis.

PAI Peptide In-Vitro Release

A device (1.25×2.00 cm, 52.0 mg) was cut from a PAI peptide-PEG-poly(DTH adipate) film loaded with 30 weight percent PAI peptide and 14 weight percent PEG ($M_w$=20,000). The release of PAI peptide was determined over a 24-hour period as described in Example 1. The release data are summarized in Table V.

TABLE V

24-HOUR IN VITRO RELEASE PROFILE OF PAI PEPTIDE FROM A DEVICE FORMULATED WITH 14 WEIGHT PERCENT OF PEG ($M_W$ 20,000 da) AND 30 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
|---|---|---|---|---|---|---|
| 15 | 4.06 | 4.06 | 23.09 | 23.09 | 0.81 | 54.19 |
| 30 | 1.25 | 5.31 | 7.09 | 30.18 | 0.25 | 16.74 |
| 45 | 0.36 | 5.67 | 2.03 | 32.21 | 0.07 | 4.77 |
| 60 | 0.26 | 5.93 | 0.47 | 33.68 | 0.05 | 3.45 |
| 90 | 0.34 | 6.28 | 1.97 | 35.66 | 0.07 | 2.32 |
| 120 | 0.25 | 6.53 | 1.42 | 37.08 | 0.05 | 1.67 |
| 150 | 0.19 | 6.72 | 1.13 | 38.21 | 0.04 | 1.32 |
| 180 | 0.14 | 6.86 | 0.80 | 39.00 | 0.03 | 0.93 |
| 240 | 0.25 | 7.12 | 1.43 | 40.44 | 0.05 | 0.84 |
| 300 | 0.18 | 7.30 | 1.02 | 41.46 | 0.04 | 0.60 |
| 420 | 0.24 | 7.53 | 1.35 | 42.81 | 0.05 | 0.40 |
| 1440 | 0.53 | 8.06 | 3.01 | 45.82 | 0.10 | 0.10 |

The device of this example is identical in all aspects to the device described in Example 3, except that the phase-disrupting polymer had a higher molecular weight. Comparison of Table V with Table IV illustrates the effect of the molecular weight of the phase-disrupting polymer on the observed release rate. In this particular example, increasing the molecular weight of the phase-disrupting polymer resulted in a reduction of the initial burst and reduction in the overall release rate over a 24-hour interval.

Mass Balance Confirmation After Completion of the Release Period

After the 24-hour release study the amount of PAI peptide entrapped in the film was released by first, removal of the device from the phosphate buffer, then dissolving the device in tetrahydrofuran (2 ml) in a 10 ml volumetric flask. After the film had completely disintegrated and a white solid was evident, the volumetric flask was filled to the 10 ml level with phosphate buffer (8.0 ml) and gently agitated. An aliquot (1 ml) was pipetted from the flask, filtered (0.45 micron syringe filter), and analyzed for PAI peptide content by HPLC. The experimentally determined amount of PAI peptide found in the film was equivalent to the amount of PAI peptide expected to be entrapped in the film based on the amount released over the 24-hour test period. This result confirms the internal consistency of the analytical methods used to measure and calculate the release of PAI peptide from release devices.

Example 5

Preparation of a 24 Weight Percent PAI Peptide Device without Phase-Disrupting Polymer Added Using the Most Preferred Methods Precipitation PAI peptide (0.14 g) was dissolved in methanol (7.0 ml). Poly(DTH adipate) (0.421 g, $M_w$=110,000) was dissolved in methylene chloride (5.0 ml). The PAI peptide solution was pipetted into the poly(DTH adipate) solution. The resulting homogeneous solution was then dripped into stirred diethyl ether (100 ml) which was cooled by a dry ice-acetone bath. A white flocculent precipitate was formed which was isolated by careful filtration using a sintered glass funnel. After drying under high vacuum at ambient temperature, a white solid material was recovered.

Film Fabrication

The completely dried PAI peptide-poly(DTH adipate) precipitate (0.41 g) was fabricated into a compression molded film as described in Example 1, using the compression profile shown in Table I. Upon removal from the mold, the film was transparent and pliable. Total PAI peptide loading was confirmed by HPLC analysis.

PAI Peptide In-Vitro Release

A device (6.3×6.7 mm, 12.4 mg) was cut from a PAI peptide-poly(DTH adipate) film loaded with 25 weight percent PAI peptide. The release of PAI peptide was determined over a 4-hour period as described in Example 1. The release data are summarized in Table VI.

TABLE VI

4-HOUR IN VITRO RELEASE PROFILE OF PAI PEPTIDE FROM A DEVICE FORMULATED WITH 25 WEIGHT PERCENT OF PAI PEPTIDE

| Time (min.) | Amt. Released (mg) | Cumul. Rel. (mg) | % Rel. | Cumul. % Rel. | Release rate in mg/cm$^2$ | Release rate in mg/cm$^2$ min |
| --- | --- | --- | --- | --- | --- | --- |
| 30 | 0.007 | 0.007 | 0.21 | 0.21 | 0.008 | 0.26 |
| 60 | 0.004 | 0.011 | 0.13 | 0.34 | 0.004 | 0.15 |
| 120 | 0.001 | 0.012 | 0.03 | 0.37 | 0.001 | 0.02 |
| 240 | 0.001 | 0.013 | 0.04 | 0.41 | 0.001 | 0.01 |

Table VI illustrates that essentially no PAI peptide release occurred over the four-hour test period. In a further study of the PAI peptide release from devices formulated without PEG, the release period was extended to 30 days. It was found that less than 5 percent of the PAI peptide loading was released over a 30-day period. This is unexpected based on teachings in the prior art, considering that PAI peptide is a hydrophilic, readily water-soluble drug. Based on prior art teachings, a 30 weight percent loading of a water-soluble drug should have resulted in a significant burst effect followed by release of the drug.

Comparative Examples

Example 6

Formulation of an EVA Release Device at a PAI Peptide Loading of 10 Weight Percent According to the Prior Art Method of Langer Film Fabrication 450 mg of EVA was dissolved in 20 ml of methylene chloride. While vigorously stirring the polymer solution, solid PAI peptide (50 mg which had previously been ground by mortar and pestle under dry conditions and sieved through a "270" mesh) was slowly added. A milky solution was formed in which the drug was well dispersed. In an atmosphere of nitrogen, the suspension was poured into a glass mold which had been pre-cooled over a dry ice-acetone mixture. The circular glass mold was covered with filter paper to facilitate the slow, overnight evaporation of the solvent. For further drying, the mold was kept under high vacuum for four hours. Then the film was separated from the mold. To remove additional traces of solvent trapped within the polymeric matrix, the film was placed between two tissue papers and kept under high vacuum at ambient temperature for a minimum of three days.

PAI Peptide In-Vitro Release

Samples were cut from the dry EVA-PAI peptide loaded films. The release of PAI peptide was determined over a four-hour period as described in Example 1. Films that were of the clinically useful thickness of 0.10–0.20 mm were characterized by excessively strong initial bursts of greater than 90 percent of the loaded PAI peptide being released in the first 10 minutes. Such films are clearly unacceptable for the development of a clinically useful device formulation.

In this example, polyethylene-vinyl acetate co-polymer (EVA) was used as a model polymer and film formulations were prepared as described in the seminal work of Langer (Siegel and Langer, *J. Contrl. Rel.*, 14, 153–67 (1990)). This is the method most commonly used in the prior art. The release profiles obtained with such films illustrate the difficulties encountered when water-soluble drugs are incorporated into polymeric films by the methods known in the prior art.

Example 7

Formulation of a Release Device at a PAI Peptide Loading of 20 Weight Percent According to the Prior Art Method of Langer Film Fabrication Poly(DTH sebacate) [a member of the family of polyarylates] and 71 mg of PAI peptide were used to prepare a suspension cast film of polymer and drug as described for Example 6.

PAI Peptide In-Vitro Release

Samples were cut from the dry poly(DTH sebacate)-PAI peptide loaded films. The release of PAI peptide was determined over a 30-day period as described in Example 1.

The film samples obtained according to Example 7 released 84 percent of the total PAI peptide loading within three hours. The remaining 16 percent of the drug loading were permanently entrapped within the film and were not released even over a 30-day period. Such formulations are clearly inferior to the systems obtained according to the preferred methods of this invention as illustrated in Examples 1 through 4.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A polymeric drug formulation consisting essentially of a single-phase dispersion of a water-soluble drug in a matrix of a water-insoluble tissue-compatible polymer that is miscible in the solid phase with said drug, wherein said single-phase dispersion is essentially free of phase-separated microdomains of drug or polymer on the length scale of visible light, so that less than five percent of the drug loading is released over a thirty day period.

2. The polymeric drug formulation of claim 1, wherein said tissue-compatible polymer is selected from the group consisting of poly(lactic acid), poly(glycolic acid), and copolymers thereof, poly(ethylene-co-vinyl acetate), poly(caprolactone), poly(orthoesters), poly(carbonates), poly(arylates) poly(imino-carbonates) poly(vinylpyrrolidone), pyran copolymer, poly(hydroxypropyl-methacrylamide-phenol), poly(hydroxy-ethylaspartamide-phenol), poly(ethylene oxide)-poly(lysine) substituted with palmitoyl residues, poly(hydroxybutyric acid), poly(acetals), poly(dihydro-pyran), poly(cyano-acrylates) and cross-linked and amphipathic block copolymers of hydrogels.

3. The polymeric drug formulation of claim 2, wherein said tissue-compatible polymer is a poly(arylate).

4. The polymeric drug formulation of claim 3, wherein said poly(arylate) is poly(desaminotyrosyl-tyrosine hexyl ester adipate).

5. The polymeric drug formulation of claim 1, wherein said water-soluble drug is a non-peptide drug selected from the group consisting of natural and unnatural antibiotics, cytotoxic agents and oligonucleotides.

6. The polymeric drug formulation of claim 1, wherein said water-soluble drug is a peptide drug selected from the group consisting of immunoglobulins, immunoglobulin fragments and platelet aggregation inhibiting peptides.

7. The polymeric drug formulation of claim 6, wherein said peptide drug is a platelet aggregation inhibiting peptide.

8. The polymeric drug formulation of claim 1, containing a drug loading up to about 50 percent by weight.

9. The polymeric drug formulation of claim 8, containing a drug loading up to about 30 percent by weight.

10. The polymeric drug formulation of claim 9, containing a drug loading between about 10 and about 20 percent by weight.

11. A method of forming a single-phase dispersion consisting essentially of a water-soluble drug in a water-insoluble tissue-compatible polymer comprising:

blending a water-soluble drug with a water-insoluble tissue-compatible polymer that is miscible in the solid phase with said drug in a solvent system capable of forming a homogenous solution of said drug and said polymer; and adding said solution to an amount of a non-solvent for said drug and said polymer, so that said drug and said polymer coprecipitate from said solution as a single-phase dispersion of said drug and said polymer;

wherein said single-phase dispersion is essentially free of phase-separated microdomains of drug or polymer on the length scale of visible light, so that less than five percent of the drug loading is released over a thirty day period.

12. The method of claim 11, wherein said tissue-compatible polymer is selected from the group consisting of poly(lactic acid), poly(glycolic acid) and copolymers thereof, poly(ethylene-co-vinyl acetate), poly(caprolactone), poly(orthoesters), poly(carbonates), poly(iminocarbonates), poly(arylates), poly(vinylpyrrolidone), pyran copolymer, poly(hydroxypropyl-methacrylamide-phenol), poly(hydroxy-ethyl-aspartamide-phenol), poly(ethylene oxide)-poly(lysine) substituted with palmitoyl residues, poly(hydroxybutyric acid), poly(acetals), poly(dihydropyran), poly(cyanoacrylates) and cross-linked and amphipathic block copolymers of hydrogels.

13. The method of claim 12, wherein said tissue-compatible polymer is a poly(arylate).

14. The method of claim 13, wherein said poly(arylate) is poly(desaminotyrosyl-tyrosine hexyl ester adipate).

15. The method of claim 11, wherein said water-soluble drug is a non-peptide drug selected from the group consisting of natural and unnatural antibiotics, cytotoxic agents and oligonucleotides.

16. The method of claim 11, wherein said water-soluble drug is a peptide drug selected from the group consisting of immunoglobulins, immunoglobulin fragments and platelet aggregation inhibiting peptides.

17. The method of claim 16, wherein said peptide drug is a platelet aggregation inhibiting peptide.

18. The method of claim 11, containing a drug loading up to about 50 percent by weight.

19. The method of claim 18, containing a drug loading up to about 30 percent by weight.

20. The method of claim 19, containing a drug loading between about 10 and about 20 percent by weight.

21. The method of claim 11, wherein said blending step comprises dissolving said water-soluble drug in a first solvent in which said drug is soluble, dissolving said tissue-compatible polymer in a second solvent in which said polymer is soluble, and combining said first and second solvent solutions, wherein said first solvent and said second solvent are capable of forming a homogeneous solution with each other and said drug and said polymer.

22. The method of claim 11, wherein said solvent system comprises at least one solvent selected from the group consisting of methanol, methylene chloride, ethanol, ethylene glycol, glycerol, tetrahydrofuran, ethyl acetate, acetonitrile, acetone, diisopropyl ether, methyl t-butyl ether, chloroform, carbon tetrachloride, dichloroethane and water.

23. The method of claim 11, wherein said drug and said polymer are each dissolved in said solvent system at a level between about 1 and about 30 percent by weight.

24. The method of claim 11, wherein said non-solvent is selected from the group consisting of diethyl ether, diisopropyl ether, methyl t-butyl ether, methyl ethyl ketone, acetonitrile, toluene, xylene and carbon tetrachloride.

25. The method of claim 11, wherein said solution of said drug and said polymer is added to at least 5 to 10 volumes of said non-solvent compared to the volume of said solvent system.

26. The method of claim 11, wherein said non-solvent is chilled to a temperature as low as the freezing point of said nonsolvent.

27. A polymeric drug formulation, prepared by the method of claim 11.

28. The polymeric drug formulation of claim 27, wherein said water-soluble drug is a platelet aggregation inhibiting peptide.

29. A blood-contacting device or implant coated with the polymeric drug formulation of claim 1, wherein said water-soluble drug is a platelet aggregation inhibiting peptide.

* * * * *